(12) United States Patent
Convert et al.

(10) Patent No.: US 9,750,643 B2
(45) Date of Patent: Sep. 5, 2017

(54) TUBULAR COMPRESSIVE ORTHOSIS

(75) Inventors: Reynald Convert, Saint Martin la Plaine (FR); Marie Gerard, Suresnes (FR); Alain Cotte, Saint Etienne (FR)

(73) Assignee: THUASNE, Levallois Perret (FR)

( * ) Notice: Subject to any disclaimer, the term of this patent is extended or adjusted under 35 U.S.C. 154(b) by 987 days.

(21) Appl. No.: 13/578,950

(22) PCT Filed: Feb. 9, 2011

(86) PCT No.: PCT/FR2011/050271
§ 371 (c)(1),
(2), (4) Date: Nov. 6, 2012

(87) PCT Pub. No.: WO2011/101578
PCT Pub. Date: Aug. 25, 2011

(65) Prior Publication Data
US 2013/0053744 A1 Feb. 28, 2013

(30) Foreign Application Priority Data
Feb. 17, 2010 (FR) ...................... 10 51119

(51) Int. Cl.
*A61F 13/06* (2006.01)
*D04B 1/26* (2006.01)
(Continued)

(52) U.S. Cl.
CPC ............. *A61F 13/08* (2013.01); *A41B 11/02* (2013.01); *A41B 11/04* (2013.01); *A41B 11/12* (2013.01);
(Continued)

(58) Field of Classification Search
CPC .......... A61F 13/00; A61F 13/04; A61F 13/06; A61F 13/061; A61F 13/08; D04B 1/22;
(Continued)

(56) References Cited

U.S. PATENT DOCUMENTS 1,529,928 A * 3/1925 Schuster .................. D04B 9/54
2/240
1,965,314 A * 7/1934 Henderson ............. A41B 11/12
2/240
(Continued)

FOREIGN PATENT DOCUMENTS

CN 1354643 A 6/2002
CN 2604894 Y 3/2004
(Continued)

OTHER PUBLICATIONS

European Patent Office, International Search Report and Written Opinion in International Application No. PCT/FR2011/050271, dated Jun. 27, 2011, with English translation of the Search Report.

Primary Examiner — Keri J Nelson
(74) Attorney, Agent, or Firm — Andrews Kurth Kenyon LLP

(57) ABSTRACT

The invention relates to a tubular compressive orthosis having an upper edge defining a first knitted compression zone, and comprising, close to said upper edge, at least one grip element facilitating the process of putting on the orthosis. Characteristically, the grip element is a second knitted gripping zone arranged beneath the upper edge and having a mesh density higher than the mesh density of the first compression zone.

19 Claims, 3 Drawing Sheets

(51) Int. Cl.
*A61F 13/08* (2006.01)
*A41B 11/04* (2006.01)
*A41B 11/12* (2006.01)
*A41B 11/02* (2006.01)
*D04B 1/18* (2006.01)
*A41B 11/00* (2006.01)

(52) U.S. Cl.
CPC ............ *A41B 11/121* (2013.01); *A61F 13/06* (2013.01); *A61F 13/061* (2013.01); *A61F 13/069* (2013.01); *D04B 1/18* (2013.01); *D04B 1/265* (2013.01); *A41B 11/00* (2013.01); *D10B 2509/028* (2013.01)

(58) Field of Classification Search
CPC .. D04B 1/24; D04B 1/26; D04B 1/265; A41B 11/00; A41B 11/02; A41B 11/04; A41B 11/12; A41B 11/121; A41B 11/123
USPC ............ 602/26, 60–63; 66/169 R, 170, 171, 66/178 R, 178 A, 182, 172 R, 173, 172 E; 2/239–242
See application file for complete search history.

(56) References Cited

U.S. PATENT DOCUMENTS

| | | | |
|---|---|---|---|
| 2,186,572 A * | 1/1940 | Boepple ................ | B21F 27/005 66/126 R |
| 3,306,081 A * | 2/1967 | Miles .................... | A41B 11/00 57/225 |
| 3,975,929 A | 8/1976 | Fregeolle | |
| 4,492,227 A * | 1/1985 | Senn et al. ...................... | 602/63 |
| 6,371,933 B1 * | 4/2002 | Gardon-Mollard ...... | D04B 9/52 2/239 |
| 6,412,311 B1 * | 7/2002 | Nakai .................... | D04B 1/102 66/64 |
| 6,430,970 B1 * | 8/2002 | Gardon-Mollard et al. ... | 66/178 A |
| 6,523,729 B1 | 2/2003 | Gardon-Mollard | |
| 6,592,539 B1 | 7/2003 | Einarsson et al. | |
| 7,017,376 B2 * | 3/2006 | Meckley ................ | D04B 1/102 66/171 |
| 7,025,738 B2 * | 4/2006 | Hall ................................ | 602/75 |
| 7,076,973 B1 | 7/2006 | Chesebro, Jr. et al. | |
| 2006/0151550 A1 | 7/2006 | Chevalier | |
| 2008/0139982 A1 * | 6/2008 | Magnusson ....................... | 602/5 |

FOREIGN PATENT DOCUMENTS

| | | |
|---|---|---|
| FR | 2775431 A1 | 9/1999 |
| FR | 2879405 A1 | 6/2006 |
| WO | 91/05498 A1 | 5/1991 |
| WO | 99/44548 A1 | 9/1999 |
| WO | 03/096851 A1 | 11/2003 |
| WO | 2008/006142 A1 | 1/2008 |

* cited by examiner

TUBULAR COMPRESSIVE ORTHOSIS

CROSS REFERENCE TO RELATED APPLICATION

This is a 371 national phase application of International Application No. PCT/FR2011/050271, filed Feb. 9, 2011, claiming priority to French application No. 1051119, filed Feb. 17, 2010, the contents of which are incorporated herein by reference in their entirety.

The present invention relates to a tubular compressive orthosis intended to improve the mechanical support given to the region of the body it covers, and proprioception.

Proprioception is the ability of the wearer to know the spatial positions and movements of body parts without the need for visual verification. This notably allows the preventing of falls and re-injury of the supported joint.

Compressive orthoses are difficult to place correctly on the joint to be strengthened. Very often, the recommended wearing of an orthosis e.g. a knee support follows after an injury preventing the wearer from fully bending or extending the joint under consideration and who is therefore hampered when putting on the orthosis.

Conventional sleeve-fit items, of pull-on type, are known having no compression effect and which comprise loops projecting from the sides or upper edge of the said sleeve-fit item so that they are easier to pull on. These loops are generally knitted loops integrated into the knit of the sleeve-fit item. These loops projecting from sleeve-fit items have the disadvantage that they may catch on surrounding objects, in particular when practicing a sport. In addition, these loops are of unpleasing appearance creating bulges under clothing for example. Finally, these loops have little resistance and pulling thereupon to put on the sleeve-fit item risks causing deterioration thereof and of the parts of the sleeve-type item onto which they are added.

Tubular compressive devices are also known, of support hosiery type, comprising a first stocking with very low coefficient of friction and a second stocking having a compressive effect. The first stocking is first placed on the leg and the second stocking is placed over the first, the fitting of the second stocking being facilitated by the sliding of the second stocking over the first stocking. The first stocking is then removed by the user from underneath the second so that only the second stocking remains fitted to the leg. These devices are complex and costly to manufacture and generally cannot be applied by persons having a leg joint with reduced mobility.

It is the objective of the present invention to propose a tubular compressive orthosis, in particular a knee orthosis, comprising at least one grip member to facilitate the fitting thereof, that is of pleasing design, solid, low-cost to manufacture, easy to use, comfortable and does not risk catching on surrounding objects.

The subject of the present invention is therefore a tubular compressive orthosis which has an upper edge delimiting a first knitted compression region and which, in the vicinity of the said upper edge, comprises at least one grip member facilitating the process of putting on the said orthosis. Characteristically, the grip member is a second knitted grasping region arranged underneath the upper edge and having a stitch density greater than the stitch density in the first compression region.

By stitch density is meant the number of columns and/or rows of stitches per centimeter or per inch.

By compression is meant any part or region of the orthosis capable of applying a compressive force [mmHg] preferably higher than 7 mmHg.

The local compressive force applied onto a limb by a compressive item is in particular a function of the force-elongation characteristics of the said item.

The pressure applied to a limb can be calculated using Laplace's law as follows:

$$P[Pa \text{ or } mmHg]=(T[N]\times n/(L[m]\times R[m])).$$

P is the pressure applied to a given point of the limb under consideration.

T is the tension expressed in Newtons applied by the said item or a part thereof when it is pulled over the lower or upper limb or trunk.

R is the radius of curvature at the point under consideration of the lower or upper limb or of the trunk.

L is the length or height of the said item or a zone thereof.

n is the number of thicknesses of the textile materials of the same item or in a zone thereof.

The compressive orthosis can be formed of a single or of several compressive zones, knitted simultaneously.

Preferably the orthosis is formed by knitting on a rectilinear loom so as to form a panel whose opposite edges are joined to form a tube.

Advantageously, the grip member is formed by the second knitted zone, arranged between the first knitted compression zone and the upper edge, so that it is fully integrated into the orthosis and comes into contact with the user's body thereby contributing towards the mechanical supporting and proprioceptive effects provided by the orthosis. The grip member also has the advantage of being resistant to pulling applied by the user.

In addition, since the stitch density is greater in the second zone than the stitch density in the first zone, this arrangement leads to a slightly greater thickness in the second zone and more rigid touch facilitating the identification and grasping thereof.

Preferably the upper edge comprises a side protruding ripple located above the said second zone. This arrangement improves the identification of and facilitates the grasping by the user of the grip member.

The said side ripple is arranged on the orthosis so that it lies on the inner or outer side of the joint to be supported when the orthosis is being worn.

This type of device facilitating grasping can also be applied to other types of orthosis such as ankle supports, wrist supports or elbow supports for example. It can also be used for compressive stockings, socks or sleeves.

The tubular orthosis according to the invention can be used as such or it can be integrated by knitting or sewing or any other equivalent means into another item such as a sock.

In one variant, the upper edge has two side protruding ripples and the orthosis comprises two second grip zones located underneath the two said ripples acting as grasping members.

The second grip zones are preferably arranged on the orthosis opposite one another so that when the orthosis is worn they lie on the inner and outer sides of the joint to be protected.

In one variant, the second zone(s) comprise an elastic knit yarn and a non-elastic knit yarn.

Since the second zones do not comprise an elastic weft yarn they do not apply a compressive force on the user's joint with which they are in contact when in use. By comparison the first compression zone necessarily comprises an elastic weft yarn to ensure a compressive effect.

Therefore the first zone comprises knitted yarns whose sum titre (dtex) of each of the said yarns is higher than the sum titre of the knitted yarns in the second zones, so that the second zones are less rigid to the touch than the first compression zone. It is possible to increase the titre of the non-elastic knit yarn in the second zone(s) so as to increase the rigidity thereof.

In one variant, the second zone(s) comprise an elastic weft yarn so as to apply a compressive effect.

Advantageously, the second zones ensure not only the function of grasping members but also the functions ensured by the first compression zone, in particular mechanical support.

In one variant, the stitch density in the second zone(s) is equal to or higher than twice the stitch density in the first compression zone with which it is connected via the knit.

The applicant has found that for optimization of the above effects, notably in terms of rigidity, the above ratio should be heeded.

In one variant, the upper edge is knitted with a single type of knit yarn, preferably non-elastic, by knitting as per the following knit structure:
- a first row of stitches knitted on all the needles of the rear needle bed;
- a second row of stitches knitted on all the needles of the front needle bed.

The upper edge is preferably knitted with a single type of knit yarn, preferably non-elastic.

In one variant, the first compression zone and the second zone(s) are knitted following one same knit structure.

This arrangement simplifies the manufacture of the orthosis and thereby reduces the cost thereof.

In one variant, the first compression zone and optionally the second zone(s) are knitted as per the following knit structure:
- a first stitch-free row along which an elastic weft yarn is inserted;
- a second row of stitches knitted in 1/1 rib stitch preferably with a non-elastic knit yarn;
- a third row of stitches knitted on the rear bed, preferably with an elastic knit yarn.

In this case, the differentiation in stitch density between the first zone and the second zone(s) is obtained by multiplying the repeat of the knit structures in each zone. For example this knit structure is repeated 16 times in the second zone(s) whereas it is repeated 8 times in the first zone.

In one variant, the elastic knit yarn has a titre equal to or higher than twice the titre of the non-elastic knit yarn, preferably the weft yarn has a titre equal to or higher than twice the elastic knit yarn.

This arrangement allows an elastic compressive orthosis to be obtained.

In one variant, the said orthosis comprises a third knitted zone arranged so that when the said orthosis is worn it covers at least the popliteal fossa, and the said third zone does not comprise an elastic weft yarn.

Preferably the third zone is knitted with an elastic knit yarn and a non-elastic knit yarn according to the invention.

The third zone having no compressive effect it does not risk causing injury by pinching or creating constriction or strangling phenomena in this region of the body containing numerous blood vessels and nerves and in which there is a thin skin layer.

In one sub-variant, the third zone comprises a stitch density that is preferably equal to or higher than twice the stitch density of the first compression zone with which it is connected via the knit.

Advantageously the third zone is formed in its entirety during the knitting of the tubular compressive orthosis so that it is not added by further manufacture onto the said orthosis. This arrangement improves user comfort and avoids contact with the skin of rigid, abrasive seams.

Preferably, the third zone extends over at least one quarter of the circumference of the tubular compressive orthosis according to the invention. This arrangement ensures user comfort whilst increasing the surface area of the orthosis available for a first compression zone, thereby improving mechanical support and proprioception.

The knit yarn(s) whether or not elastic, and the elastic weft yarn(s), can be multi-filament or monofilament yarns, simple or gimped with one or more multifilament yarns which may or may not be twisted, or one or more monofilaments.

The present invention will be better understood on reading an example of embodiment which is non-limiting and illustrated by the following Figures appended hereto and in which.

Figure 1:
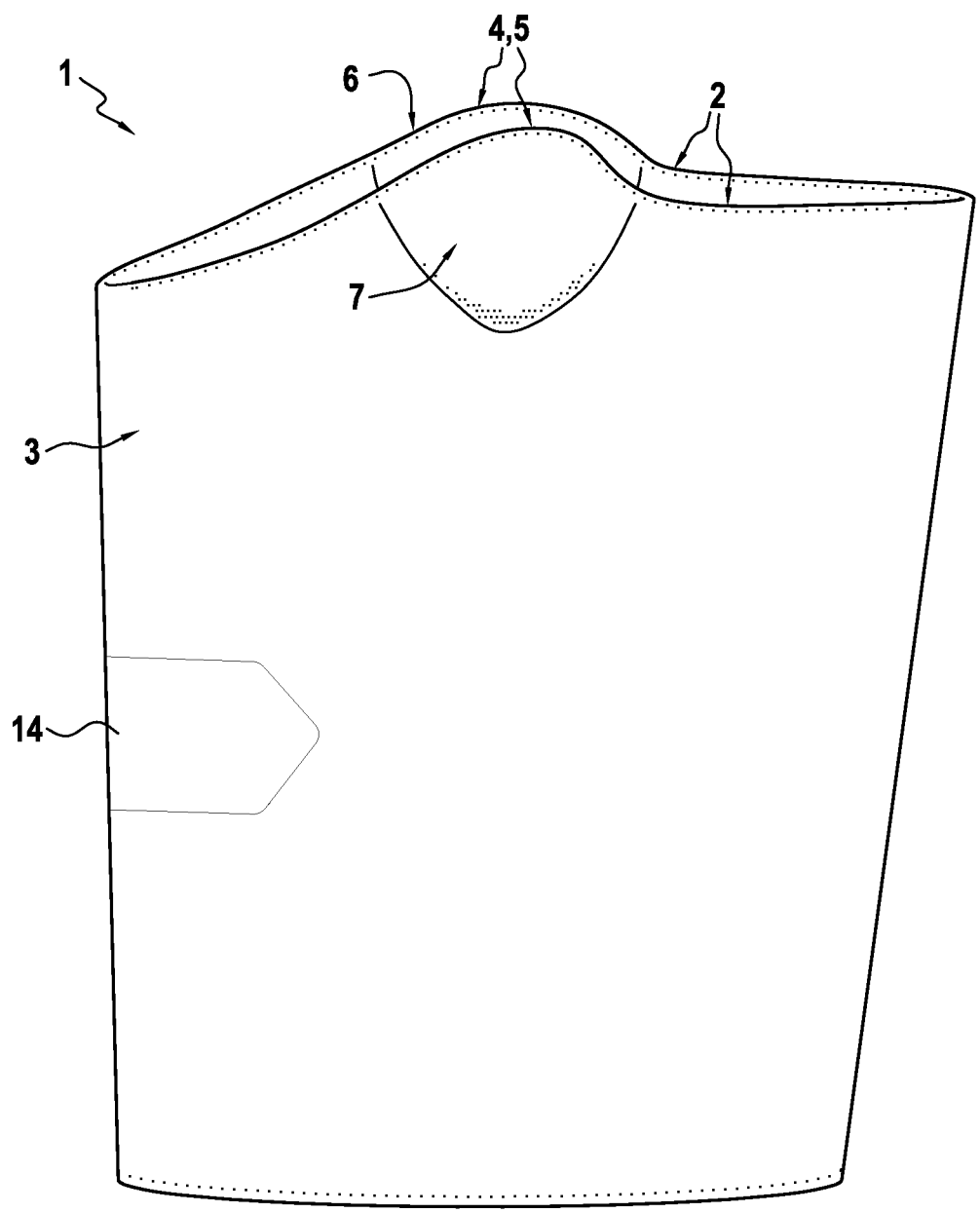
FIG. 1 is a side view of an example of a compressive orthosis according to the invention.

The tubular compressive orthosis 1 illustrated in FIG. 1 is a knee support having an upper edge 2 delimiting a first knitted compression zone 3. The said upper edge 2 has two protruding side ripples 4, 5 arranged opposite one another so that they lie on the inner and outer sides of the user's knee when the knee support is being worn. The orthosis 1, in the vicinity of the said edge 2, comprises two second grip zones 6, 7 located underneath the said ripples 4, 5 and hence underneath the said upper edge 2. These second grip zones 6, 7 act as grasping members.

Figure 2:
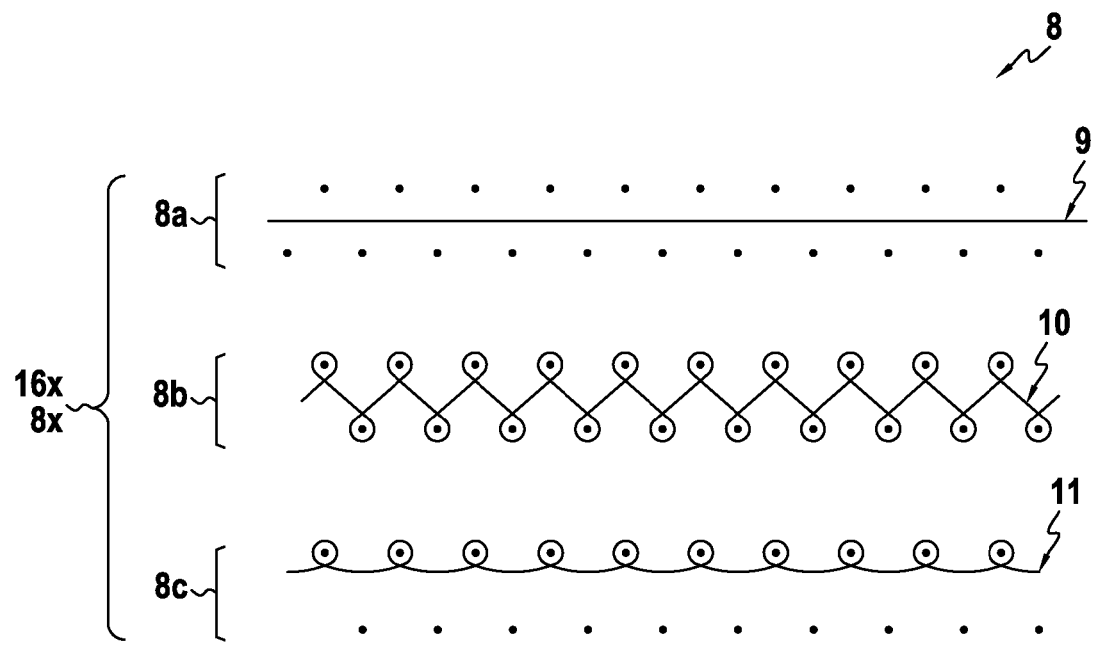
FIG. 2 illustrates a first knit structure.

Preferably the second grip zones 6, 7 are knitted following the same knit structure as the first compression zone 3. The knit structure 8 illustrated in FIG. 2 comprises:
- a first stitch-free row 8a along which an elastic weft yarn 9 is inserted;
- a second row 8b of stitches knitted in 1/1 rib stitch preferably with a non-elastic knit yarn 10;
- a third row 8c of stitches knitted on the rear needle bed, preferably with an elastic knit yarn 11.

The second 8b and third 8c rows of stitches can be locally reversed on the orthosis 1.

The first compression zone 3 and the second grip zones 6, are therefore advantageously knitted during one same knitting step using an elastic knit yarn 11, a non-elastic knit yarn 10 and an elastic weft yarn 9. The knit structure 8 is repeated eight times in the first compression zone 3 compared with sixteen times in the second grip zones 6, 7 which contributes to obtaining a stitch density in the second zones 6,7 equal to or higher than twice the stitch density in the first compression zone 3. Also, the characteristic according to which the first compression zone 3 comprises an elastic weft yarn 9 also allows the compressing and hence tightening of the columns and/or rows of stitches in the second compression zones 6, 7 thereby contributing towards increasing the stitch density in the said second zones.

This differentiation in stitch density and the protruding shape of the second grip zones 6, 7 facilitate the identification and gripping of the said second zones 6, 7 by the user.

In addition, the second zones 6, 7 form an integral part of the orthosis 1 and do not project beyond it, thereby preventing them from catching or even tearing and contributing towards the mechanical support effect and proprioception effect provided by the orthosis 1. Since the second zones 6, 7 comprise elastic weft yarns 9 they also contribute towards the compressive effect provided by the orthosis 1.

It is also possible to omit the elastic weft yarn 9 in the second zones 6, 7 so that they are more flexible.

Figure 3:
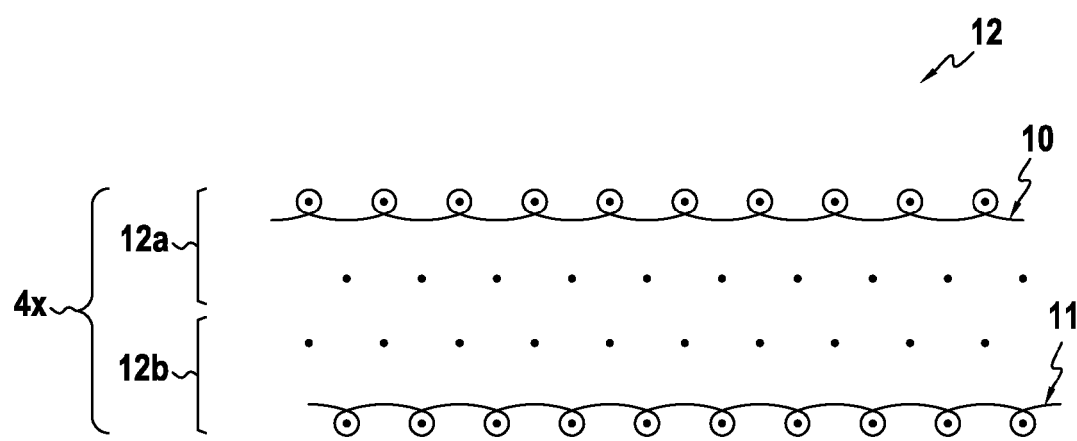
FIG. 3 illustrates a second knit structure.

The upper edge 2 is knitted at the same time as the first compression zone 3 and the second grip zones 6, 7 as per the following knit structure 12 illustrated in FIG. 3:
- a first row 12a of stitches knitted on all the needles of the rear bed using a non-elastic knit yarn 10;
- a second row 12b of stitches knitted on all the needles of the front bed using an elastic knit yarn 11.

The knit structure 12 is preferably repeated four times at the said upper edge 2.

Preferably the compressive orthosis 1 is entirely formed by rectilinear knitting of a panel, then the opposite side edges are joined along a seam 13 to form a tube.

The orthosis 1 also comprises, on its posterior face 1b, a third knitted zone 14 arranged to cover the popliteal fossa when it is being worn. This third zone 14 also comprises an elastic knit yarn 11 and a non-elastic knit yarn 10. The third zone 14 does not comprise an elastic weft yarn which prevents injury to the region of the fragile popliteal fossa. The stitch density in the third zone 14 is greater than the density of the first compression zone 3, preferably equal to or more than twice that of the first compression zone 3. The third zone 14 is therefore knitted following the knit structure 8 illustrated in FIG. 2 except that it does not comprise an elastic weft yarn 9 and the second row 8b of stitches is reversed with the third row 8c of stitches, as in the first compression zone 3 surrounding the said third zone 14 with which it is connected via the knit.

Figure 4:
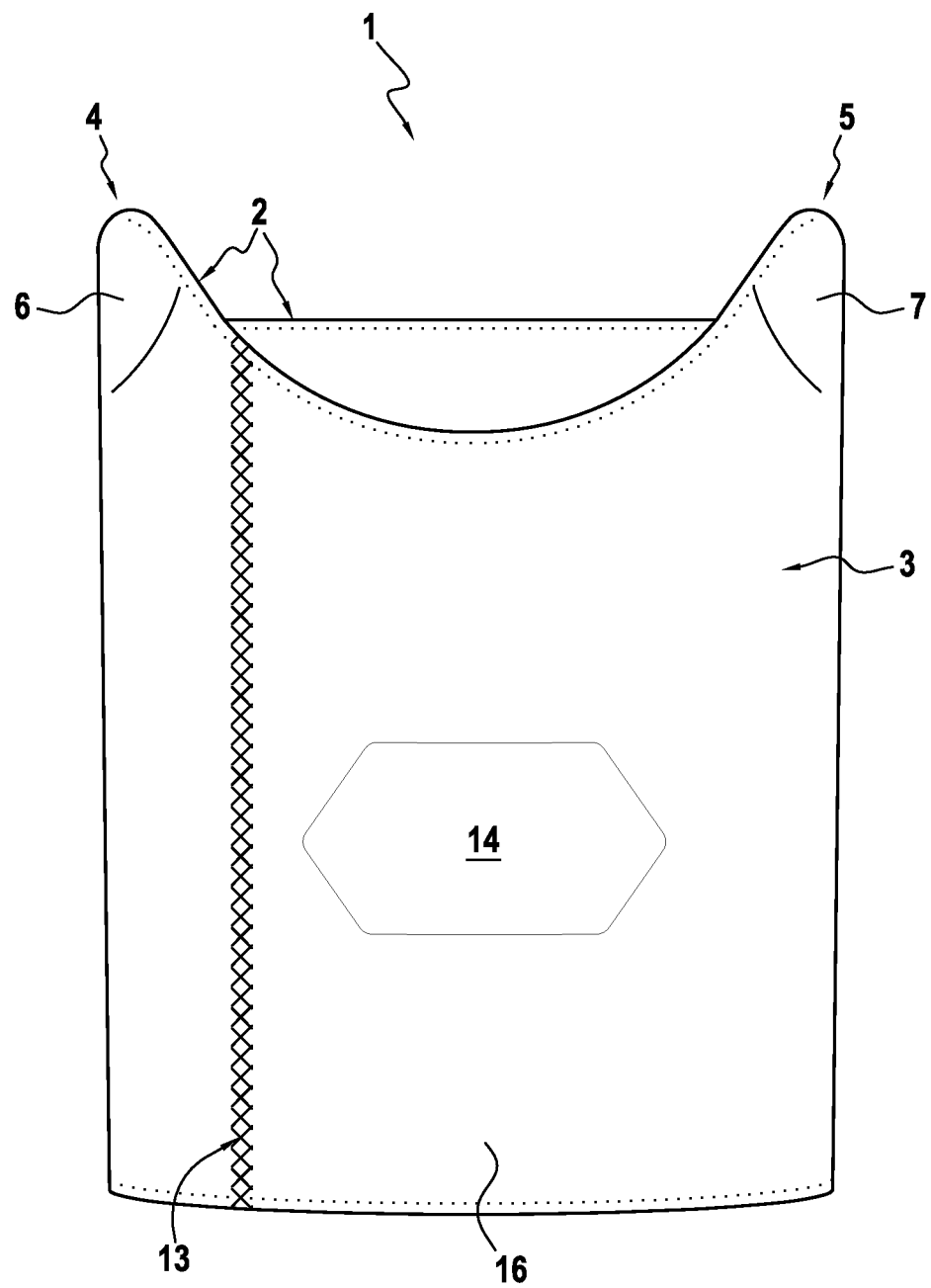
FIG. 4 is a view of the rear side of the compressive orthosis illustrated in FIG. 1.

In this particular example and as illustrated in FIGS. 1 and 4, the third zone 14 extends over at least one quarter of the circumference of the orthosis 1.

In the first compression zone 3, the second grip zones 6, 7 and the third zone 14 covering the popliteal fossa, the elastic knit yarn 11 has a titre that is at least twice higher than that of the non-elastic knit yarn 10, and the weft yarn 9 has a titre equal to or more than twice the titre of the elastic knit yarn 11. As a precise example, the non-elastic knit yarn 10 has a titre of the order of 150 detxt, the elastic knit yarn 11 has a titre of the order of 400 dtex and comprises a double elastic core yarn gimped with non-elastic yarns, and the weft yarn 9 has a titre of the order of 900 dtext and comprises a double elastic monofilament gimped with non-elastic multifilament yarns.

It is possible to increase the rigidity of the second zones by increasing the titre of the elastic knit yarn 11, in particular of the elastic core monofilament.

The invention claimed is:

1. A tubular compressive orthosis having an upper edge delimiting a first knitted compression zone comprising a first stitch density and comprising a first elastic knit yarn, a first non-elastic knit yarn, and a first elastic weft yarn so as to apply a compressive effect, and which, in the vicinity of the said upper edge, comprises at least one first grip member facilitating the process of putting on the said orthosis, wherein the first grip member is a second knitted grip zone comprising a second stitch density and comprising a second elastic knit yarn and a second non-elastic knit yarn, which is arranged underneath the upper edge, said second stitch density being greater than said first stitch density, wherein the first and second stitched densities are defined by the number of columns and/or rows of stitches per centimeter or per inch, wherein said at least one first grip member is arranged between the first knitted compression zone and the upper edge, and wherein said at least one first grip member and the first knitted compression zone are of unitary knitted construction, and wherein the upper edge comprises a side protruding ripple located above the said second zone improving the identification of and facilitating the grasping by the user of the first grip member.

2. The orthosis according to claim 1, wherein the upper edge has first and second side protruding ripples and delimits a second knitted compression zone comprising a third stitch density, and wherein the orthosis comprises in addition to said first grip member, a second grip member which is a third knitted grip zone comprising a fourth stitch density and arranged underneath the upper edge, between the second knitted compression zone and the upper edge, and wherein said fourth stitch density is greater than said third stitch density, the third and fourth stitched densities being defined by the number of columns and/or rows of stitches per centimeter or per inch, wherein said second grip member and the second knitted compression zone are of unitary knitted construction, said first grip member being located underneath the first side protruding ripple and said second grip member being located underneath the second side protruding ripple, and wherein said first and second grip members act as grasping members.

3. The orthosis according to claim 2, wherein the third knitted grip zone comprise an elastic knit yarn and a non-elastic knit yarn.

4. The orthosis according to claim 3, wherein the third knitted grip zone comprise an elastic weft yarn so as to apply a compressive effect.

5. The orthosis according to claim 4, wherein the elastic knit yarn has a titre equal to or higher than twice the titre of the non-elastic knit yarn and wherein the weft yarn has a titre equal to or higher than twice the titre of the elastic knit yarn.

6. The orthosis according to claim 2, wherein the fourth stitch density in the third knitted grip zone is equal to or higher than twice the third stitch density in the second knitted compression zone with which it is connected via the unitary knitted construction.

7. The orthosis according to claim 2, wherein the second knitted compression zone and the third knitted grip zone are knitted following one same knit structure.

8. The orthosis according to claim 2, wherein the second knitted compression zone and optionally the third knitted grip zone further comprise the following knit structure:
- a first stitch-free row along which an elastic weft yarn is inserted;
- a second row of 1/1 rib knitted stitches;
- a third row of knitted stitches on a rear face of the second knitted compression zone and optionally on a rear face of the third knitted grip zone with an elastic knit yarn;

and wherein the second and third rows can be reversed.

9. The orthosis according to claim 1, wherein the second knitted grip zone comprises a second elastic weft yarn so as to apply a compressive effect.

10. The orthosis according to claim 9, wherein the elastic knit yarn has a titre equal to or higher than twice the titre of the non-elastic knit yarn and wherein the weft yarn has a titre equal to or higher than twice the titre of the elastic knit yarn.

11. The orthosis according to claim 1, wherein the second stitch density in the second knitted grip zone is equal to or higher than twice the first stitch density in the first knitted compression zone with which it is connected via the knitted construction.

12. The orthosis according to claim 1, wherein the upper edge is knitted with a single type of knit yarn, the upper edge comprising rows of stitches and columns of stitches and having a front face and a rear face, the upper edge having the following knit structure:
- a first row of stitches knitted on all the columns of the rear face;
- a second row of stitches knitted on all the columns of the front face.

13. The orthosis according to claim 12, wherein the single type of knit yarn is non-elastic.

14. The orthosis according to claim 1, wherein the first knitted compression zone and the second knitted grip zone are knitted following one same knit structure.

15. The orthosis according to claim 1, wherein the first knitted compression zone, and optionally the second knitted grip zone, comprise(s) rows of stitches and columns of stitches, and has/have a front face and a rear face, the first knitted compression zone and optionally the second knitted grip zone further comprise the following knit structure:
- a first stitch-free row along which an elastic weft yarn is inserted;
- a second row of 1/1 rib knitted stitches;
- a third row of knitted stitches on the rear face;
and wherein the second and third rows can be reversed.

16. The orthosis according to claim 15, wherein the second row of stitches is knitted with a non-elastic knit yarn.

17. The orthosis according to claim 1, wherein it comprises a third knitted zone arranged so that, when the said orthosis is being worn, it covers at least the popliteal fossa and wherein the said third zone does not comprise an elastic weft yarn.

18. The orthosis according to claim 17, wherein the third zone has a fifth stitch density equal to or greater than twice the first stitch density of the first compression zone with which it is connected via the knit.

19. The orthosis according to claim 1, wherein the second stitch density is at least twice as dense as the first stitch density.

* * * * *